*United States Patent* [19]

Kontos et al.

[11] Patent Number: 5,180,367

[45] Date of Patent: Jan. 19, 1993

[54] PROCEDURE AND BALLOON CATHETER SYSTEM FOR RELIEVING ARTERIAL OR VEINAL RESTRICTIONS WITHOUT EXCHANGING BALLOON CATHETERS

[75] Inventors: Stavros B. Kontos, Woodcliff Lake; Jeffrey C. Urbanski, Sparta, both of N.J.

[73] Assignee: Datascope Corporation, Paramus, N.J.

[21] Appl. No.: 759,612

[22] Filed: Sep. 16, 1991

Related U.S. Application Data

[63] Continuation of Ser. No. 403,498, Sep. 6, 1989, abandoned.

[51] Int. Cl.$^5$ .............................................. A61M 25/10
[52] U.S. Cl. ....................................... 604/101; 606/194; 604/243
[58] Field of Search .............. 606/191, 192, 194; 604/95–103, 243

[56] References Cited

U.S. PATENT DOCUMENTS

| | | | |
|---|---|---|---|
| 4,299,226 | 11/1981 | Banka | 128/344 |
| 4,468,224 | 8/1984 | Enzmann et al. | 604/247 |
| 4,616,648 | 10/1986 | Simpson | 128/303 R |
| 4,655,746 | 4/1987 | Daniels et al. | 604/101 |
| 4,744,366 | 5/1988 | Jang | 128/344 |
| 4,748,982 | 6/1988 | Horzewski et al. | 128/344 |
| 4,762,129 | 8/1988 | Bonzel | 128/344 |
| 4,763,654 | 8/1988 | Jang | 128/344 |
| 4,824,435 | 4/1989 | Giesy et al. | 606/191 |
| 4,846,174 | 7/1989 | Willard et al. | 606/194 |
| 4,911,163 | 3/1990 | Fina | 604/101 |
| 4,917,088 | 4/1990 | Crittenden | 606/194 |
| 5,035,686 | 7/1991 | Crittenden et al. | 604/96 |

FOREIGN PATENT DOCUMENTS

WO86-06285 11/1986 PCT Int'l Appl. .
WO88-00844 2/1988 PCT Int'l Appl. .
2180454 4/1987 United Kingdom .

OTHER PUBLICATIONS

USCI Cataloge, 1968, p. 3.
American Journal of Cardiology, "A New Catheter System for Coronary Angioplasty", Simpson et al., Apr. 1, 1982.

*Primary Examiner*—C. Fred Rosenbaum
*Assistant Examiner*—William W. Lewis
*Attorney, Agent, or Firm*—Fitzpatrick, Cella, Harper & Scinto

[57] ABSTRACT

The invention described is a procedure whereby a small balloon catheter can be placed in a patient's body, expanded and collapsed as needed and then a second, larger balloon catheter placed over the smaller one. There is also disclosed a balloon catheter system for performing the above-noted procedure.

17 Claims, 6 Drawing Sheets

PROCEDURE AND BALLOON CATHETER SYSTEM FOR RELIEVING ARTERIAL OR VEINAL RESTRICTIONS WITHOUT EXCHANGING BALLOON CATHETERS

This application is a continuation of application Ser. No. 07/403,498 filed Sep. 6, 1989, now abandoned.

BACKGROUND OF THE INVENTION

1. Field of the Invention

Generally, this invention relates to a medical procedure for enlarging the cross sectional area of a section of a fluid flow passageway. The invention also covers the system for performing said procedure.

Specifically, the most common medical procedure to which the instant invention relates is a percutaneous transluminal coronary angioplasty procedure, hereinafter referred to by its commonly accepted shorthand designations "PTCA" or "angioplasty." Angioplasty is most frequently called for when blood flow through one or more coronary arteries is severely restricted as the result of the accumulation of plaque deposits on the artery walls.

An accumulated deposit which results in the constriction or narrowing of the flow path is called a stenosis. The object of angioplasty is to enlarge or dilate the stenosis, and the procedure is normally accomplished by use of dilatation catheters.

2. Description of the Prior Art

An article entitled "A New Catheter System For Coronary Angioplasty" by Simpson et al, published in the American Journal of Cardiology (Apr. 1, 1982) describes the general angioplasty procedure in some detail. Numerous patents have issued, particularly over the past five years, describing a wide variety of catheters, methods for inserting and placing catheters and methods for performing angioplasty. Among those most relevant to the instant invention are U.S. Pat. Nos. 4,762,129 (Bonzel), 4,748,982 (Horzewski and Yock), 4,616,648 (Simpson); 4,468,224 (Enzmann and Lundquist), British Patent No. 2,180,454 and PCT applications having Publication Numbers WO 88/00844 and WO 86/06285.

SUMMARY OF THE INVENTION

As noted above, angioplasty involves enlarging or dilating a restricted or stenotic region of a coronary artery or vessel. This is generally accomplished by inserting a dilatation catheter into the vascular system, feeding it through that system until the balloon at the distal end is within the stenosis. As used herein, the terms "distal" and "proximal" are as viewed from the vantage point of the physician who is inserting the device. In other words, the end of the catheter which remains outside of the patient's body is the proximal end and the working end, the one with the balloon that is placed within the stenosis, is the distal end.

Once the balloon is within the stenosis, fluid, often contrast medium, under pressure is introduced through the catheter tube into the balloon chamber. The expansion of the balloon chamber tends to compress the stenosis against the vascular wall. Thereafter, reducing the pressure and thereby collapsing the balloon leaves an enlarged flow path for the passage of blood.

Often, however, the procedure must be repeated one or more times with successively larger balloons. It is frequently the case that the stenosis is so large and the restriction so severe that only the smallest balloon, commonly known as a predilatation catheter, and referred to herein as a pilot balloon or pilot catheter, can be placed within the affected region. That pilot balloon, however, may not be large enough to dilate the stenosis sufficiently to permit adequate blood flow therethrough. However, by using a pilot balloon to begin the enlarging process, room is made to allow insertion of a larger diameter PTCA balloon.

Thus, in performing an angioplasty procedure, it is frequently found necessary or at least highly advantageous to remove the small diameter catheter and replace it with a larger one. U.S. Pat. No. 4,616,648 describes this catheter exchange procedure and covers a device to facilitate same.

In performing angioplasty a physician will often first introduce a guide wire into the vascular system and feed it through the vascular tree until the end is in or through the stenosis. Then the balloon catheter, most commonly of a dual lumen design, will be passed over the guide wire and will follow that wire to the stenotic region. Thereafter, when the exchange of balloons is to be made, the first catheter is removed, leaving the guide wire in place, and the second catheter is then fed over the wire to the stenotic region.

In order to accomplish that exchange employing traditional techniques, the guide wire must extend outside of the patient's body a distance at least equal to the length of the catheter. Generally, such a guide wire may be on the order of 300 cm., with half that length or more outside the body. A dangling guide wire of that length outside the body presents obvious problems. It can get in the way of those performing the procedure. It can easily fall to the floor and become contaminated. In addition, it is much more difficult to manipulate than is a shorter one.

In an attempt to overcome these problems, British patent No. 2,180,454 describes a two-piece detachable guide wire system which permits removal of the long external portion of the guide wire when it is no longer needed.

U.S. Pat. Nos. 4,762,129 (Bonzel) and 4,748,982 (Horzewski and Yock) propose to solve the problem by reconfiguring the balloon catheter so that the guide wire need not pass through the entire length thereof. In this way, they say, the procedure can be performed with a much shorter guide wire.

All of these proposed solutions, however, still require an exchange of balloons, i.e., removal of one balloon before insertion of the next. The present applicant(s), on the other hand, have taken an entirely different approach. Instead of exchanging catheters, the instant invention contemplates permitting the pilot catheter to remain resident in the vascular system, with the balloon portion thereof, if desired, still within the stenotic region, while feeding the second, larger diameter PTCA catheter over the pilot catheter.

The procedure of the instant invention requires less manipulation of devices within the vascular system and hence reduces the risk of trauma. It also permits insertion of the predilatation or pilot catheter alone without giving up the ability to insert a PTCA catheter thereafter except by catheter exchange. In addition, the long guide wire is no longer needed.

The instant inventors are not, however, the only persons to have tried to obviate the need to exchange balloons. U.S. Pat. Nos. 4,744,366 and 4,763,654, both issued to G. David Jang, reflect other such efforts in this direction. Both those patents teach the use of a multilumen multi-balloon catheter in which the balloons are all co-axial. In the '654 patent the balloon elements are in tandem, i.e. they are longitudinally displaced, one from another, whereas in the '366 patent at least two of the balloons are concentric, with one entirely within the chamber of another.

The devices of those Jang patents appear to have their own drawbacks. It is expected that they may be expensive and difficult to fabricate. In addition, where the balloons are longitudinally displaced, it might be necessary, in order to locate the larger balloon within the stenosis, to push the smaller balloon farther beyond the stenosis than the physician might want to do. With the concentric balloon configuration (the '366 patent) the fully collapsed balloons cannot be made as small as a collapsed pilot balloon alone.

Another system designed to obviate the need for catheter exchange is shown in PCT application having Publication No. WO 88/00844. That application discloses a true dual lumen PTCA catheter through which there can be inserted a small diameter predilatation catheter. However, the PTCA catheter must be inserted either before or simultaneously with the predilatation catheter. The latter cannot be inserted first. Moreover, when inserting the predilatation catheter of that application, the balloon membrane must pass through the entire length of the inner lumen of the PTCA catheter.

At least one drawback to this system and procedure is that it requires insertion of the large diameter PTCA catheter every time the smaller catheter is to be used. It also calls upon the physician to anticipate in which of his/her cases there is likely to be difficulty in advancing the large diameter PTCA catheter. If such difficulties are not anticipated, this system is not recommended. Unfortunately, the state of the art of fluoroscopy is not far enough advanced to make such predictions entirely reliable. With the instant invention, however, because the pilot catheter is inserted first, it is anticipated that its system and procedure can be employed irrespective of whether difficulties are anticipated.

The other PTC application identified above (Publication No. WO 86/06285) has similar disclosure and is subject to the same limitations and drawbacks as those discussed in connection with PCT application WO 88/00844.

The instant invention covers a catheter system and a medical procedure wherein a balloon exchange is made unnecessary, which system and procedure, however, are different from and avoid the drawbacks of those disclosed in the above-noted Jang patents and in the PCT applications.

In traditional angioplasty procedures, physicians often use, in addition to or instead of a guide wire, a guide catheter. The use of such a guide catheter is shown in U.S. Pat. No. 4,299,226 (Banka). The instant invention permits the continued use of guide catheters. Indeed, it also contemplates, if the physician so desires, the continued use of a guide wire to locate the first or pilot catheter. That guide wire may remain resident in the pilot catheter or it can be removed, depending upon the preference of the physician, without in any way affecting the practice of the instant invention.

Although the description herein is being made primarily in the context of an angioplasty procedure because that is where it is believed the invention will have the most immediate and widespread applicability, it should be understood that the invention itself is not so limited. It may have application to any procedure wherein the size of a fluid flow passage must be increased.

DETAILED DESCRIPTION OF THE DISCLOSED EMBODIMENTS

Figure 1:
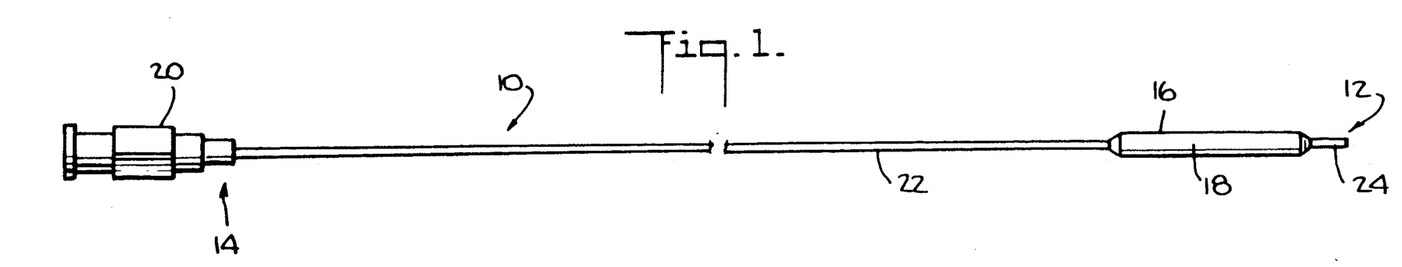
FIG. 1 is a side elevational view of a first, small diameter, pilot balloon catheter useful in practicing the instant invention.

A pilot catheter 10 useful in practicing the instant invention has a distal end 12 and a proximal end 14. At or near the distal end there is located an inflatable balloon membrane 16. Detachably affixed in fluid-tight fashion to the proximal end is a female luer-type fitting 20. Running from fitting 20 to balloon 16 is a hollow catheter tube 22. The lumen of tube 22 opens into fitting 20 at one end and into balloon chamber 18 at the other. The distal end may also be provided with a flexible steering tip 24 to facilitate proper feeding and placement.

Fitting 20 is designed to accept, in fluid tight fashion, means, for example, a syringe (not shown), for forcing fluid under pressure into the lumen of tube 22. The application of such pressure causes balloon membrane 16 to expand and define chamber 18. Removing that source of fluid pressure and applying a partial vacuum causes the balloon membrane to collapse.

In the preferred embodiment for practicing the instant invention, fitting 20 is made to be removable from and reattachable to tube 22. Alternatively, and still within the scope of the invention, fitting 20 can be removed from tube 22 by cutting the latter.

Figure 11:
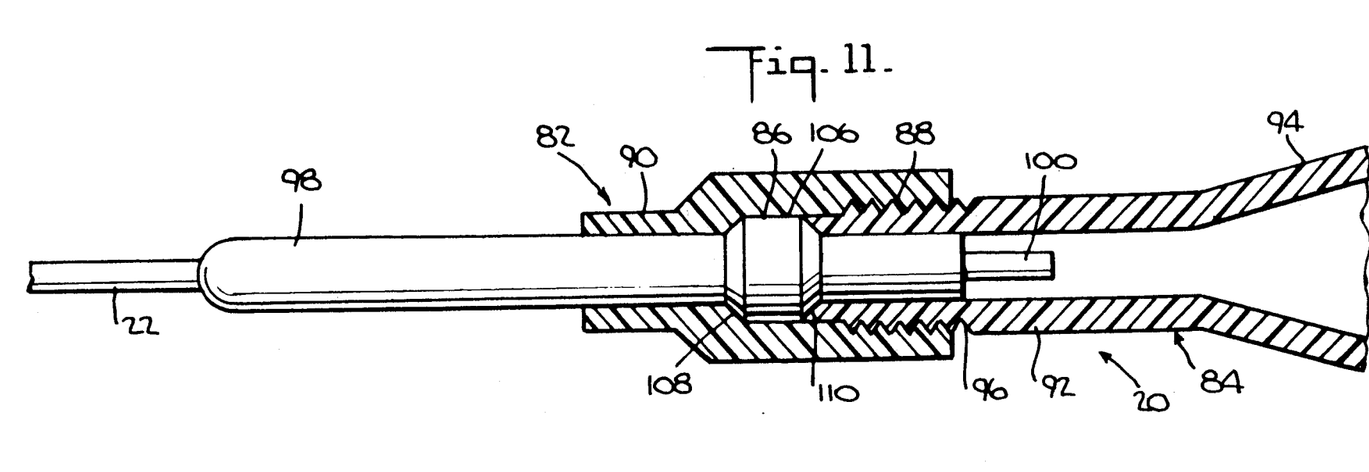
FIG. 11 is a cross sectioned side elevation of a removable liner fitting useful in practicing the invention.

Suitable structure for removable fitting 20 is shown in FIG. 11. It has a compression cap 82 and a luer lock body 84. Cap 82 has a hollow passageway therethrough with a large diameter proximal segment 86 having an internal thread 88 and a smaller diameter distal segment 90. Body 84 also has a hollow passageway therethrough with the distal segment 92 thereof being cylindrical and the proximal end 94 being frusto-conically shaped so as to accept, in fluid-tight engagement, fluid-pressure generating means such as a syringe (not shown).

Body 84 is also provided with an external thread 96 at its distal end to engage thread 88 in cap 82. When body 84 is threaded into cap 82 their respective through passages are coaxial and in communication with one another.

Figure 12:
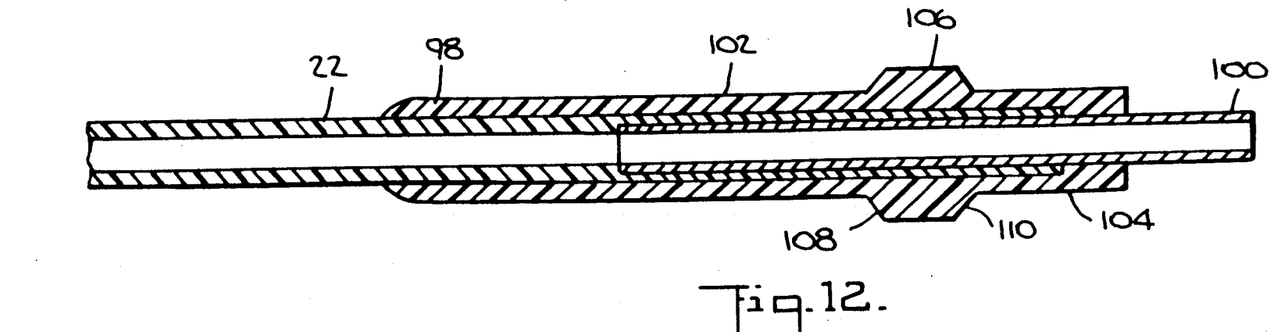
FIG. 12 is an enlarged cross sectioned side elevation of the proximal end of the catheter tube and compression sleeve assembly of FIG. 10.

As best seen in FIG. 12, a deformable compression sleeve 98 is provided to fit over catheter tube 22. In addition, steel reinforcing tube 100 is provided to fit inside the proximal end of tube 22.

Sleeve 98 has a distal cylindrical portion 102, a proximal cylindrical portion 104 and an enlarged head or seal portion 106 between the two.

Cylindrical portion 102 is sized to slide in distal segment 90 of the passage through cap 82. Cylindrical portion 104 of sleeve 98 is sized to slide in distal segment 92 of the passageway of body 84. Seal 106, however, is too large to fit into either segment 90 or segment 92.

Seal 106 has converging sloping faces 108 and 110. The transition from proximal segment 86 to distal segment 90 of the passageway through cap 82 is by means of a taper having the same slope as that of face 108 of seal 106. Similarly, the distal end of the passageway through body 84 is provided with an internal taper having the same slope as that of face 110 of seal 106.

Because of the above-described geometry, when body 84 is threaded tightly into cap 82, seal 106 is compressed inwardly against catheter tube 12 to form a fluid-tight seal. Steel tube 100 is provided to prevent collapse of tube 12 when the seal is compressed against it.

In order to remove fitting 20, cap 82 is rotated counter-clockwise relative to body 84 in order to relieve the compressive force on seal 106. Then the entire fitting assembly, including sleeve 98, is slid off catheter tube 22.

As mentioned above, the procedure and system of the subject invention can be employed in conjunction with or without a guide wire. The fitting of FIG. 11 is for use without a guide wire. If a guide wire is to be used, a Y fitting would be employed instead of the straight fitting of FIG. 11. Such a Y fitting would have a second compressive seal proximal to the leg of the Y and could also incorporate means for grabbing and manipulating the guide wire. Suitable structure for a Y fitting of that type is disclosed in co-pending application entitled "Angioplasty Balloon Catheter with Captive Safety Guide" application Ser. No. 403,497 being filed concurrently herewith by one of the instant inventors.

Figure 2:
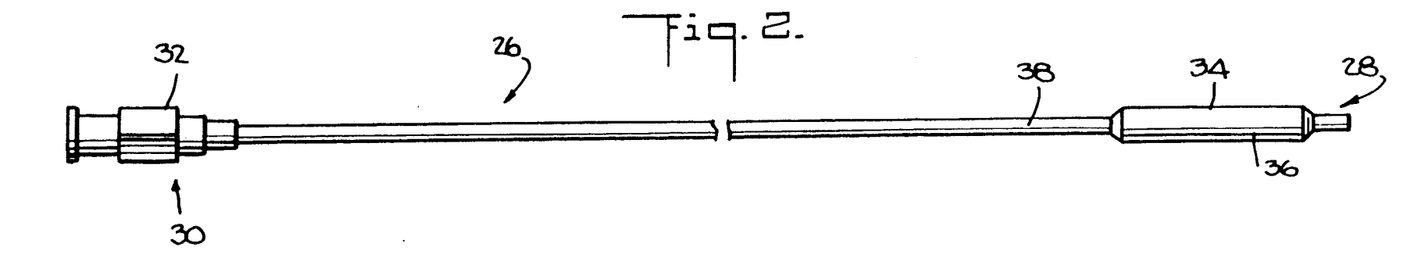
FIG. 2 is a side elevational view of a second, larger diameter, balloon catheter useful in practicing the instant invention.

The second, larger diameter catheter 26 is of somewhat similar design to that of pilot catheter 10. It has a distal end 28 and a proximal end 30. At the proximal end is another female luer-type fitting 32 similar to fitting 20, but one which is not removable. At or near distal end 28 is a second balloon membrane 34, and between fitting 32 and balloon 34 is hollow catheter tube 38. The lumen of tube 38 opens into fitting 32 at one end and into balloon chamber 36 at the other.

As with the pilot catheter, the second balloon membrane 34 can be expanded by application of fluid under pressure to the lumen of tube 38, thereby to define chamber 36. Such can be accomplished by connecting fluid pressure application means, for example, a syringe (not shown), to fitting 32.

Figure 3:
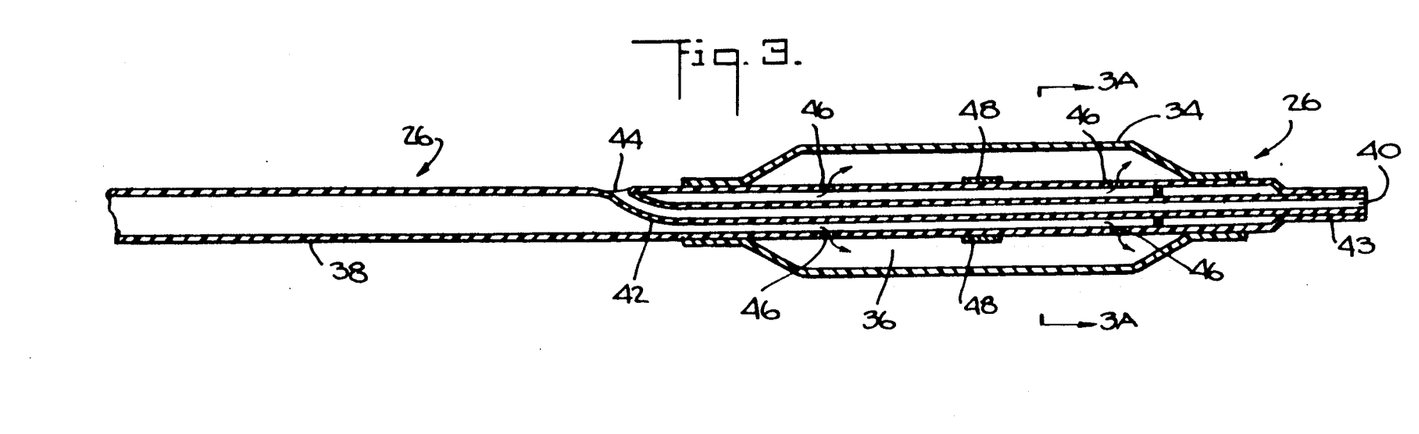
FIG. 3 is an enlarged side elevation, with parts cut away, of the distal end of the catheter depicted in FIG. 2.
Figure 3A:
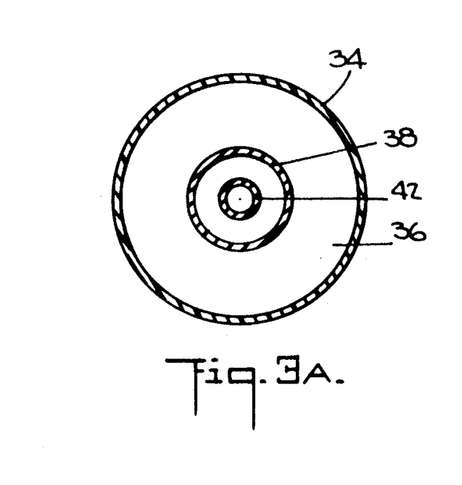

At distal end 28 of catheter 26 short outer sliding guide means 42, in the form of a hollow tube, are provided. As seen in FIG. 3, these sliding guide means run through the interior of balloon chamber 36. Communication between the lumen of tube 38 and chamber 36 is accomplished by providing ports 46 in that portion of tube 38 which is within the chamber.

Sliding guide means 42, are depicted in FIG. 3 as running through the interior of tube 38 from the tip end 40 through chamber 36 and exiting at 44 through the wall of tube 38 just proximate to the proximal end of membrane 34. Alternatively, the sliding guide means 52 (FIGS. 4 and 4A) can start at tip end entrance 50, thence run, within chamber 36, alongside of tube 41 in region X and ending at 54 immediately upon exiting from the proximal end of chamber 36.

Figure 4:
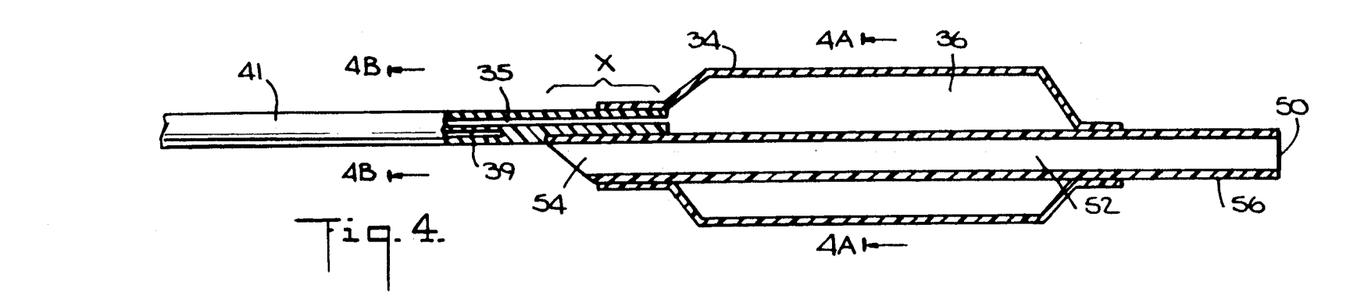
FIG. 4 is an enlarged side elevation, with parts cut away, of an alternative embodiment of the distal end of a second, larger diameter, balloon catheter useful in practicing the instant invention.
Figure 4A:
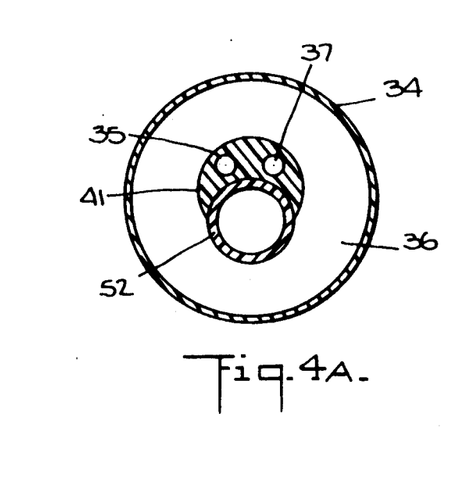
FIG. 4A is a cross sectional view of the catheter of FIG. 4 taken along cutting line 4A—4A.
Figure 4B:
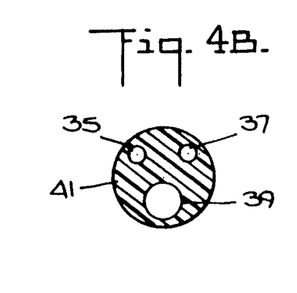

The catheter tube 41 shown in FIG. 4 has multiple lumens 35, 37 and 39. Lumens 35 and 37 communicate with chamber 36 for expanding and collapsing membrane 34. Lumen 39 can be made to accommodate a stiffening wire (not shown). The stiffening wire can be made to be removable, thereby to enable the physician to vary the flexibility of the PTCA catheter to accommodate to the needs of the particular case. The stiffening wire can also serve to transmit at least some of the axial force necessary to advance the balloon through the arterial tree. To facilitate use of the stiffening wire it is believed most advantageous to taper its distal end from the main body diameter, which may range from about 0.012 inches to 0.016 inches, down to as small as about 0.004 inches.

Figure 5:
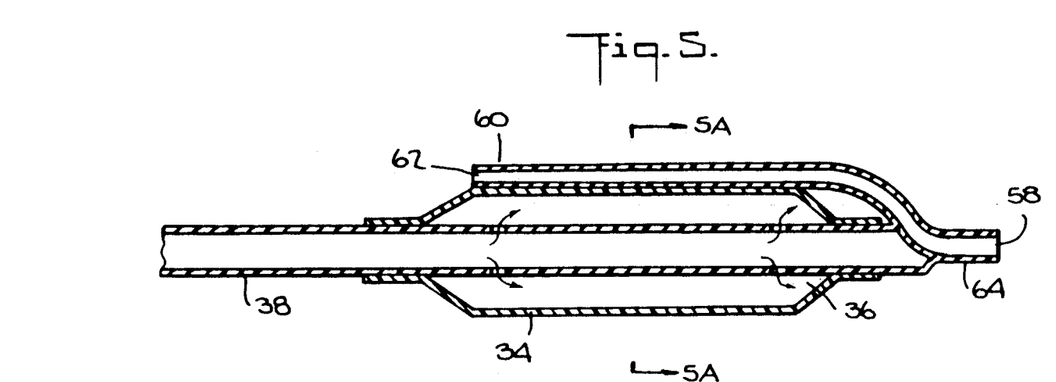
FIG. 5 is a side elevational view, with parts cut away, of another alternative embodiment of the distal end of a second, larger diameter, balloon catheter useful in practicing the invention.
Figure 5A:
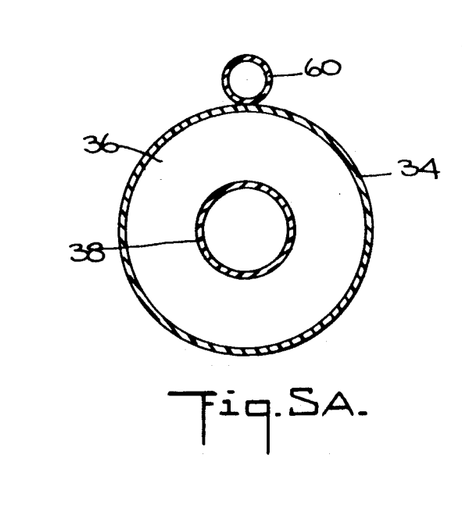
FIG. 5A is a cross-sectional view of the catheter of FIG. 5 taken along cutting line 5A—5A.

A second alternative embodiment is depicted in FIGS. 5 and 5A, where the sliding guide means 60 begins at tip 58, terminates at 62, immediately adjacent the proximal end of chamber 36. In this embodiment, the sliding guide means 60 runs along the outside of membrane 34.

As can be seen in the embodiments of FIGS. 3, 4 and 5, the flexible distal tip portion (43, 56 and 64 respectively) can form part of the sliding guide means.

Figure 6:
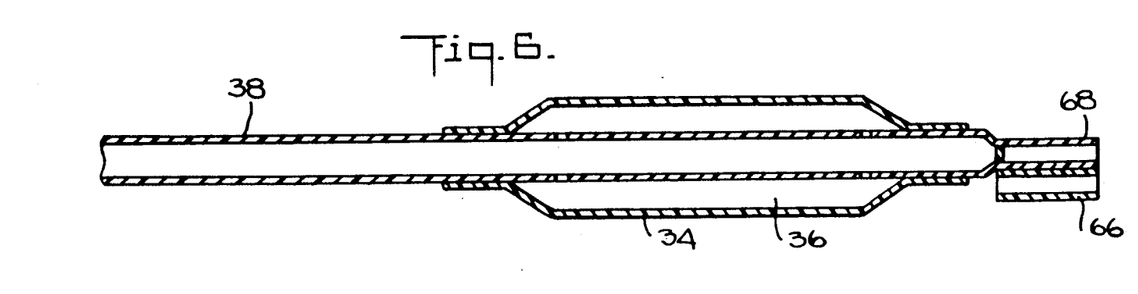
FIG. 6 is a side elevational view, with parts cut away, of yet another alternative embodiment of the distal end of a second, larger diameter, balloon catheter useful in practicing the instant invention.

FIG. 6 depicts yet another embodiment. In this one, the sliding guide means 66 are extremely short, perhaps 0.25 inches, extending only about the length of the flexible tip 68 and running alongside thereof.

Figure 7:
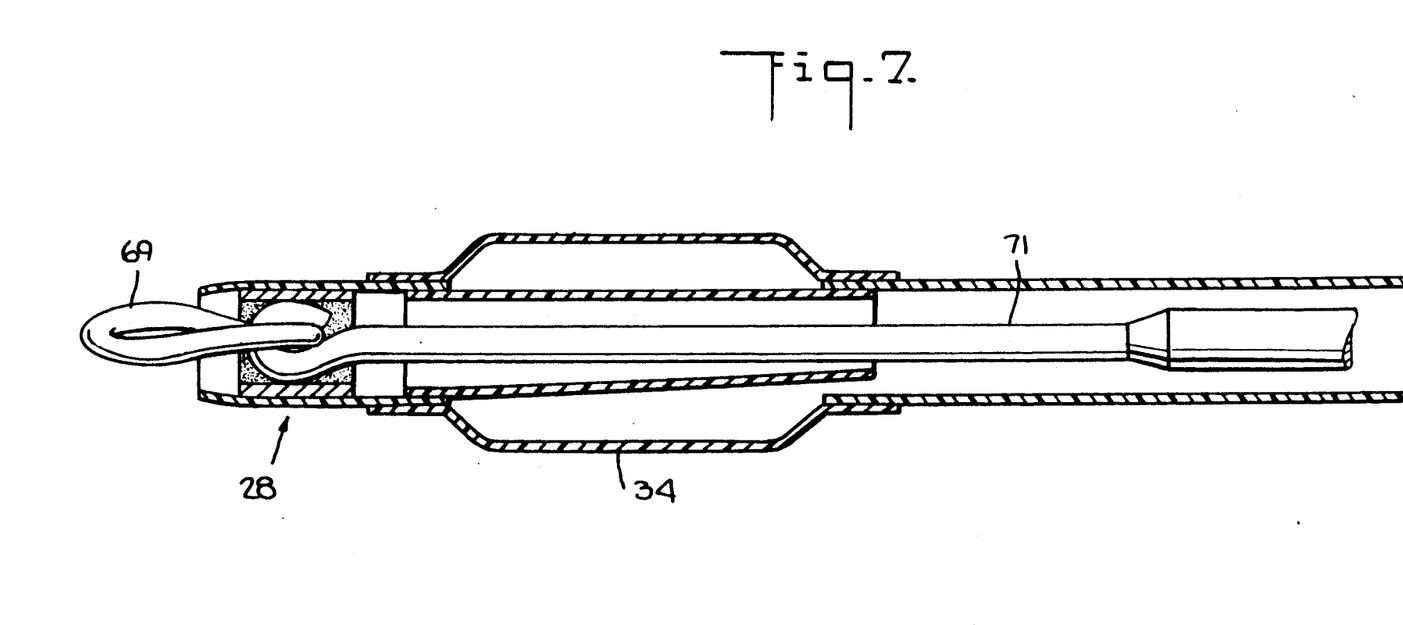
FIG. 7 is a side elevational view, with parts cut away, of yet another alternative embodiment of the second, larger diameter, balloon catheter useful in practicing the instant invention.

Perhaps the limit in shortening the sliding guide means is shown in FIG. 7. In that embodiment the sliding guide means consists of a small loop 69. While the loop could be in the form of a rigid ring of fixed dimension made, for example, of stainless steel or hard plastic, it may be preferable for it to be of flexible material. Biocompatible plastic line of between 0.002 and 0.10 inches O.D. would be suitable. The loop material could be affixed to the distal end of a resident push-support wire 71. It is believed most desireable for the wire 71 to be rotatable and axially moveable within tip 28.

Although several alternative forms of sliding guide means are shown in the FIGS., one feature they all have in common is that each is much shorter than the catheter tube/balloon combination with which it operates. It is anticipated that the sliding guide means will never be longer than about 50% of the overall length of the entire device, and seldom, if ever, longer than 20% of that length. Instead, normally the sliding guide means will be only slightly longer than the length of the balloon chamber. Because the sliding guide means are short, most of the main body of the pilot catheter will be outside of the PTCA catheter.

Irrespective of the form of sliding guide means employed, if it is of fixed dimension, the passageway through it must be so sized as to permit the pilot balloon and catheter tube to slide easily therein. In a typical system embodying the instant invention with a fixed dimension sliding guide means, the inside diameter of sliding guide means 52 might be about 0.034 inches and the outside diameter of pilot tube 22 about 0.032 inches. Pilot balloons range from about 0.020 to 0.030 inches when collapsed, and from as small as about 0.060 inches to as large as about 0.160 inches when fully expanded. The larger or PTCA balloon might range from about 0.047 inches to 0.060 inches when collapsed and from about 0.080 inches to about 0.160 inches when fully expanded. The outside diameter of the second tube 38 might be about 0.040 inches.

The method of the instant invention begins with the introduction of the pilot catheter into the vascular system, frequently into the femoral artery. Preparation of the pilot catheter and its introduction into the vascular system are done in the conventional manner well known to those in the field. It is then fed through the vascular system until the balloon membrane 16 is located within the stenosis. Fluid pressure application means, normally a syringe, are then connected to fitting 20 and fluid, under pressure, is forced into the lumen of tube 22, thereby expanding membrane 16 and creating chamber 18. Once the stenosis has been compressed as much as the pilot balloon can compress it, pressure is removed from the lumen of tube 22 and a partial vacuum applied in order to fully collapse membrane 16. A determination is then made as to whether further dilatation is necessary, possible or would be advantageous. If it is, the procedure continues. The syringe is then disconnected from fitting 20, and fitting 20 itself is removed from tube 22. Alternatively, fitting 20 can remain connected to the syringe and the two can be disconnected from tube 22 as a unit.

Figure 8:
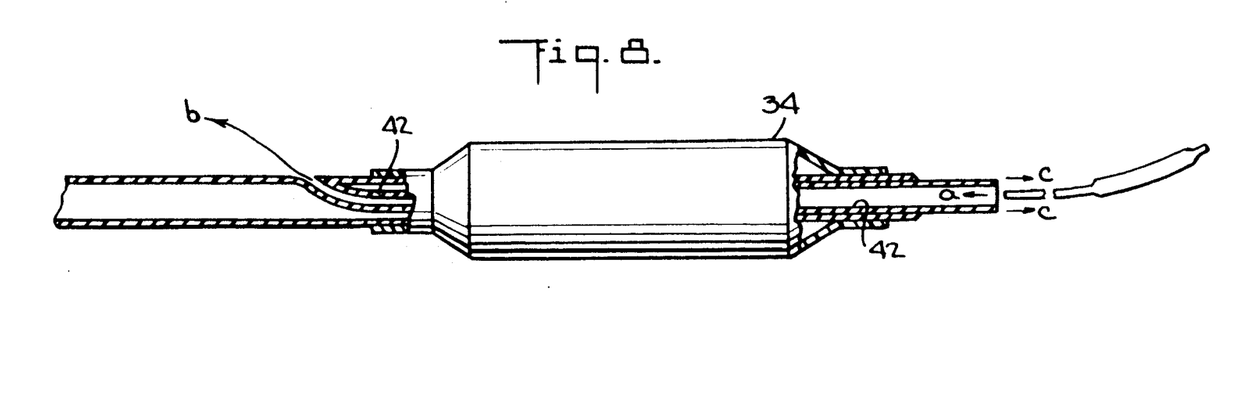
FIG. 8 is a side elevational view, with parts cut away, of the distal end of the catheter of FIG. 2 showing how it is passed over a pilot catheter.
Figure 9:
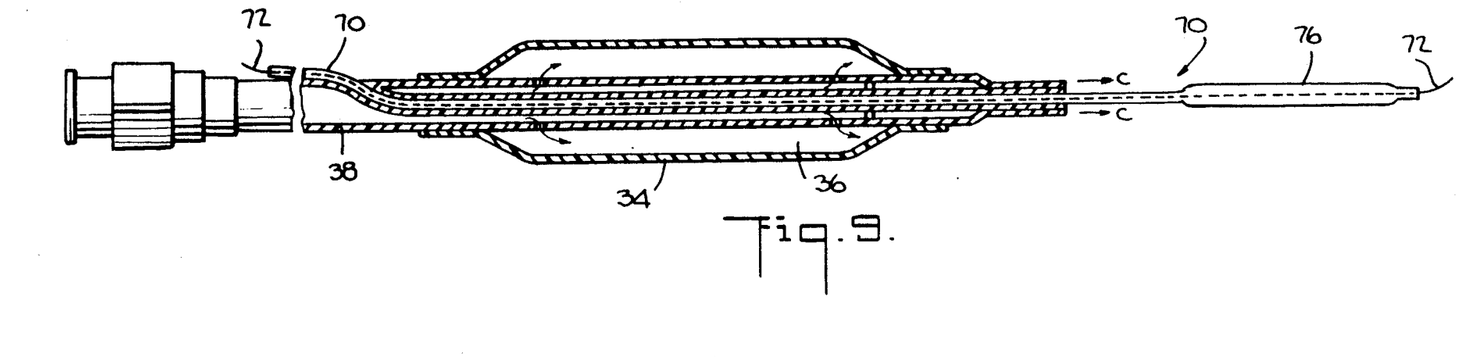
FIG. 9 is a side elevational view of a pilot catheter as the distal end of the second catheter is sliding along same.

Proximal end 14 of pilot catheter 10, with fitting 20 having been removed therefrom, is then fed into the distal end of the sliding guide means, entering the distal end thereof (arrow "a") and exiting the proximal end (arrow "b") as shown in FIG. 8. As depicted in FIG. 9, the second catheter is then fed into the vascular system with the sliding guide means riding along the pilot tube, as indicated by arrows "c", until the second balloon 34, following the path of the pilot catheter 10, reaches the stenosis. Confirmation of proper location of the second balloon can be made through the use of fluoroscopy. For this purpose, a radio opaque marker 48 is placed on tube 38. In the embodiment depicted, marker 48 is shown as being located within chamber 36, but it could also be placed just distally to or proximally of the chamber. A radio opaque marker can also be provided on pilot catheter 10 for the same purpose.

Balloon membrane 34 is then expanded in the same manner as was described above with respect to expanding membrane 16. Once the stenosis has been fully compressed, pressure is removed and a partial vacuum applied to the lumen of tube 38. The two catheters can then be removed, either together or one at a time, as the physician may prefer.

An alternative procedure is to use an indwelling guide wire 72 to facilitate placement of the pilot catheter. In that event, a dual lumen pilot catheter 70 would be employed. A typical guide wire might have a 0.014 inch diameter and the guide wire lumen of catheter 70 might have an inside diameter of 0.016 inches. Steerable guide wires 78, including those with coils 80 at their distal ends, can also be used. The insertion of the guide wire can precede insertion of the pilot catheter, the two can be inserted together as a unit, or the guide wire can be inserted after the pilot balloon is in the vascular system, all in accordance with well known techniques.

Preferably, however, instead of passing the pilot catheter over an indwelling guide wire, it is contemplated that the pilot catheter will be provided with a captive safety guide that is axially and rotationally movable relative to the balloon. In order to present the smallest profile when the pilot balloon is collapsed, it is believed advantageous to reduce the diameter of that segment of the pilot tube which passes through the balloon chamber. While the inside diameter of the main body of the pilot tube may be about 0.024 inches, that might be reduced to as small as about 0.007 inches as it passes through the balloon chamber. If the inside diameter of the pilot tube is made too small, passing it over an indwelling guide wire becomes impractical. It is believed, therefore, that in the preferred embodiment, the pilot catheter should have a captive safety guide. However, it should be understood that the instant invention is not so limited as to require a captive guide wire or, indeed, a guide wire at all.

In using the instant invention as depicted in the embodiment of FIG. 7, the pilot catheter 10 would pass through loop 69. To promote as much flexibility as possible and accommodate the needs of as many different conditions as possible, the size of loop 69 can be adjusted and its orientation varied. Pulling wire 71 in the proximal direction shortens loop 69 and forces the PTCA catheter 26 to follow the path of the pilot catheter 10 more closely. Conversely, extending the wire 71 distally lengthens loop 69 and permits the physician greater leeway in maneuvering the second catheter. The longer loop also slides more easily over pilot catheter 10.

Figure 10:
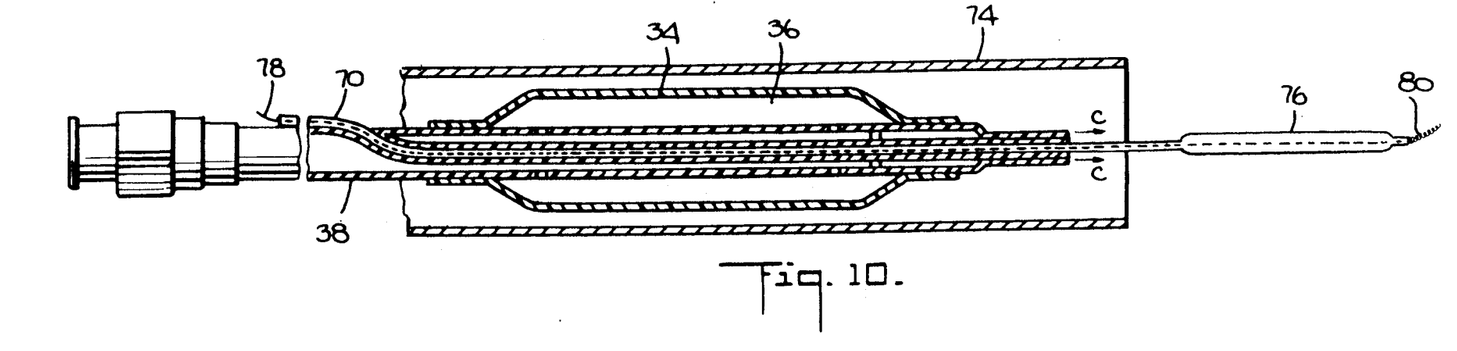
FIG. 10 is a side elevational view of a guiding catheter, with the pilot catheter tube, over a guide wire, resident therein, as the distal end of the second catheter is sliding along the pilot catheter tube.

Yet another alternative would be to introduce a guide catheter 74 into the vascular system before or simultaneously with introduction into the vascular system of the pilot catheter. A guide catheter can be used with a guide wire, as depicted in FIG. 10, or without one. A guide wire may be employed without a guide catheter as depicted in FIG. 9, or with one, as depicted in FIG. 10. The guide catheter is fed into the vascular system until its distal end is in the vicinity of the stenosis. Pilot catheter 70 is then fed through the guide catheter until membrane 76 exits from the distal end thereof. Pilot catheter 70 is then fed further along until membrane 76 is within the stenosis. Expansion and collapse of the pilot balloon then proceed as described above, as does removal of fitting 20. The proximal end of pilot catheter 70 is then fed through the guide means of the second catheter and the second catheter is fed along the pilot catheter, through guide catheter 74, as shown in FIG. 10, until membrane 34 exits from the distal end of guide catheter 74. Placement, expansion and collapse of membrane 34 then proceed as described above.

When using a guide catheter, removal is preferably accomplished by withdrawing both dilatation catheters until membranes 76 and 34 are within the guide catheter. Then all three elements can be removed as a unit. However, the present invention contemplates removal in other ways as well. The guide catheter can be removed first, followed by one dilatation catheter or the other (or both as a unit). Alternatively, one or the other of the dilatation catheters (or both together as a unit) can be removed before the guide catheter.

As mentioned above, both an indwelling guide wire and a guide catheter can be used in practicing the invention. The guide wire 72 can be inserted first, then the guide catheter 74 over it. A dual lumen pilot catheter 70 would then be fed over guide wire 72 and through guide catheter 74 until the pilot balloon is within the stenosis. The pilot balloon would then be expanded to reduce the stenosis and the balloon then would be collapsed.

Once the stenosis has been compressed by the pilot balloon, fitting 20 is removed and the proximal end of the pilot tube is fed through the guide means of the second or PTCA catheter. The second catheter is then fed along the pilot catheter, through guide catheter 74 (as shown in FIG. 10) in the same manner as described above in connection with FIG. 9. Again, with respect to the scope of the instant invention, the sequence of removal of pilot catheter, second catheter, guide wire and guide catheter is of no moment. Indeed, the guide wire and/or the guide catheter can even be removed before introduction into the vascular system of the second catheter.

As yet another alterative, if the physician so desires he may put the two catheters together and then insert them as a unit into the artery. Normally this would be accomplished by placing the pilot catheter through the sliding guide means while the two catheters are outside the patient's body, leaving enough of the pilot catheter protruding distally of the guide means so as to be able to function as a flexible safety guide. The unit could than be inserted into the artery and advanced through the arterial system in more or less conventional fashion.

The instant invention also contemplates using the disclosed system to enlarge more than one stenosis. After the first stenosis has been fully compressed, as described above, the second catheter balloon membrane 34 is withdrawn from the treated region by sliding guide means 52 in a proximal direction along pilot tube 22. Fitting 20 is then reattached to proximal end 14 of pilot catheter 10 and pilot catheter 10 can then be manipulated so as to place its balloon membrane within a second stenosis, either in the same artery or in a different one. Expansion and collapse of pilot balloon 20 then proceed as described above. Thereafter, if needed, sliding guide means 52 of the second catheter are slid distally over pilot tube 22 (and, if need be, over membrane 16) until membrane 34 is within the second stenosis. Again, expansion and collapse of balloon membrane 34 proceed as described above.

While the method and system of this invention have been described above in connection with several specific embodiments, it should be understood that numerous modifications could be made by persons of skill in this art without departing from the scope of this invention. Accordingly, the above description is intended to be merely illustrative and not limiting. The scope of the invention claimed should be understood as including all those alternatives and modifications which the above specification would readily suggest or which would readily occur or be apparent to one skilled in the art upon reading the above.

What is claimed is:

1. A system for performing a medical procedure comprising:
    a) a first, relatively small diameter, balloon catheter having a catheter portion, a balloon portion, a proximal end and a distal end, with said balloon portion being located at or near said distal end, in said passageway;
    b) removable fitting means at or near the proximal end of said first balloon catheter for attachment thereto of fluid pressure application means;
    c) a second, larger diameter balloon catheter having a catheter portion, a balloon portion, a proximal end, a distal end, with said balloon portion being located at or near said distal end,
    d) sliding guide means at or near the distal end of said second balloon catheter, said sliding guide means having a distal end and a proximal end with a passageway therethrough from the distal to the proximal end thereof, which passageway is of such size as to accommodate therein and permit sliding passage therethrough of the balloon portion and the catheter portion of said first balloon catheter, said sliding guide means being not longer than about ½ the overall length of said second balloon catheter and is comprised of a ring at the distal end of said second balloon catheter.

2. A system for performing a medical procedure comprising:
    a) a first, relatively small diameter, balloon catheter having a catheter portion, a balloon portion, a proximal end and a distal end, with said balloon portion being located at or near said distal end, said first balloon catheter has a captive safety guide;
    b) removable fitting means at or near the proximal end of said first balloon catheter for attachment thereto of fluid pressure application means;
    c) a second, larger diameter balloon catheter having a catheter portion, a balloon portion, a proximal end, a distal end, with said balloon portion being located at or near said distal end;
    d) sliding guide means at or near the distal end of said second balloon catheter, said sliding guide means having a distal end and a proximal end with a passageway therethrough from the distal to the proximal end thereof, which passageway is of such size as to accommodate therein and permit sliding passage therethrough of the balloon portion and the catheter portion of said first balloon catheter, said sliding guide means being not longer than about ½ the overall length of said second balloon catheter.

3. A system for performing a medical procedure comprising:
    a) a first, relatively small diameter, balloon catheter having a catheter portion, a balloon portion, a proximal end and a distal end, with said balloon portion being located at or near said distal end;
    b) removable fitting means at or near the proximal end of said first balloon catheter for attachment thereto of fluid pressure application means;

c) a second, larger diameter balloon catheter having a catheter portion, a balloon portion, a proximal end, a distal end, with said balloon portion being located at or near said distal end;

d) sliding guide means at or near the distal end of said second balloon catheter, said sliding guide means having a distal end and a proximal end with a passageway therethrough from the distal to the proximal end thereof, which passageway is of such size as to accommodate therein and permit sliding passage therethrough of the balloon portion and the catheter portion of said first balloon catheter, said sliding guide means being not longer than about ½ the overall length of said second balloon catheter and is comprised of a flexible loop at the distal end of said second balloon catheter.

4. The system of claim 1, 2 or 3 wherein said fitting can be reattached to said first balloon catheter.

5. The system of claim 1, 2 or 3 wherein said sliding guide means are not longer than 1/5 the overall length of the second balloon catheter.

6. The system of claim 1, 2, or 3 wherein said second balloon chamber has a distal end and a proximal end and wherein the distal end of said sliding guide means is located at or near the distal end of the second balloon chamber and the proximal end of the sliding guide means is located at or near the proximal end of the second balloon chamber.

7. The system of claim 3 wherein said flexible loop is of variable size at the distal end of said second balloon catheter.

8. A method for performing a medical procedure involving enlarging the flow passage of a section of a fluid passageway within the patient's body comprising:

a) placing a first, relatively small diameter balloon catheter in said passageway;
said first balloon catheter having a catheter portion and a balloon portion and a proximal end and a distal end, with said balloon portion located at or near said distal end,
said first balloon catheter having a fitting at or near its proximal end for connection thereto of fluid pressure application means, b) advancing said first balloon catheter through said passageway until said balloon portion is located within said section to be enlarged, c) expanding the balloon portion of said first balloon catheter by forcing fluid under pressure through the catheter portion thereof into the balloon chamber, d) reducing the pressure in said first balloon catheter and withdrawing fluid from and thereby collapsing said first balloon chamber prior to feeding said second balloon portion into said passageway section, e) removing said fitting from said first balloon catheter, f) placing a second, larger diameter balloon catheter over the catheter portion of said first balloon catheter,
said second balloon catheter having a catheter portion and balloon portion and a proximal end and a distal end, with said balloon portion located at or near said distal end,
said second balloon catheter further having sliding guide means near said distal end, which sliding guide means is so sized and positioned as to accommodate therein and permit sliding passage therethrough of the balloon portion and the catheter portion of said first balloon catheter,
said sliding guide means being further characterized in that it has a distal end and a proximal end and is not longer than about ½ the overall length of said second balloon catheter, g) feeding the proximal end of the catheter portion of said first balloon catheter through said sliding guide means, from the distal end thereof to the proximal end thereof, and continuing to feed said second balloon catheter into said passageway and along said first balloon catheter until said balloon portion of said second balloon catheter is within the passageway section to be enlarged, h) expanding the balloon portion of said second balloon catheter by forcing fluid under pressure through the catheter portion thereof into the balloon chamber thereof, i) reducing the pressure in said second balloon catheter and withdrawing fluid from and thereby collapsing the balloon chamber thereof, and j) retracting the balloon portion of said second balloon catheter from said section of said fluid passageway, k) relocating the balloon portion of said first balloon catheter from said second section of said fluid passageway, l) expanding the balloon portion of said first balloon catheter, m) reattaching said fitting to said first balloon catheter before expanding the balloon portion thereof, n) collapsing the balloon portion of said balloon catheter, o) sliding said sliding guide means along the catheter portion of said first balloon catheter until the balloon portion of said second balloon catheter is within said second fluid passage section, p) expanding the balloon portion of said second balloon catheter;

q) collapsing the balloon portion of said second balloon catheter, and r) removing said first balloon catheter and said second balloon catheter from said passageway.

9. The method of claim 8 wherein said fitting can be removed and reattached to said first balloon catheter, further comprising the step of reattaching said fitting to said first balloon catheter after the proximal end thereof has been passed through said guide means.

10. The method of claim 8 wherein the catheter portion of said second balloon catheter has a blind or partially blind stiffening wire lumen therein and wherein a stiffening wire is provided, further comprising the steps of advancing the second balloon catheter through said vein or artery by applying at least some axial force to said stiffening wire.

11. The method of claim 8 or 9 wherein said sliding guide means are not longer than 1/5 the overall length of said second balloon catheter.

12. The method of claim 9 wherein said second balloon chamber has a distal end and a proximal end and wherein the distal end of said sliding guide means is located at or near the distal end of the second balloon chamber and the proximal end of the sliding guide means is located at or near the proximal end of the second balloon chamber.

13. A method for performing a medical procedure involving enlarging the flow passage of a section of a fluid passageway within the patient's body comprising:

a) placing a first, relatively small diameter balloon catheter in said passageway;
   said first balloon catheter having a catheter portion and a balloon portion and a proximal end and a distal end, with said balloon portion located at or near said distal end,
   said first balloon catheter having a fitting at or near its proximal end for connection thereto of fluid pressure application means,
b) advancing said first balloon catheter through said passageway until said balloon portion is located within said section to be enlarged,
c) expanding the balloon portion of said first balloon catheter by forcing fluid under pressure through the catheter portion thereof into the balloon chamber,
d) reducing the pressure in said first balloon catheter and withdrawing fluid from and thereby collapsing said first balloon chamber prior to feeding said second balloon portion into said passageway section,
e) removing said fitting from said first balloon catheter,
f) placing a second, larger diameter balloon catheter over the catheter portion of said first balloon catheter,
   said second balloon catheter having a catheter portion and balloon portion and a proximal end and a distal end, with said balloon portion located at or near said distal end,
   said second balloon catheter further having sliding guide means near said distal end, which sliding guide means is so sized and positioned as to accommodate therein and permit sliding passage therethrough of the balloon portion and the catheter portion of said first balloon catheter,
   said sliding guide means being further characterized in that it has a distal end and a proximal end and is not longer than about ½ the overall length of said second balloon catheter, wherein the catheter portion of said second balloon catheter has a stiffening wire lumen therein and wherein a removable stiffening wire is provided, further comprising the steps of inserting said stiffening wire in said stiffening wire lumen when reduced flexibility is desired and removing or partially retracting said stiffening wire when increased flexibility is desired,
g) feeding the proximal end of the catheter portion of said first balloon catheter through said sliding guide means, from the distal end thereof to the proximal end thereof, and continuing to feed said second balloon catheter into said passageway and along said first balloon catheter until said balloon portion of said second balloon catheter is within the passageway section to be enlarged,
h) expanding the balloon portion of said second balloon catheter by forcing fluid under pressure through the catheter portion thereof into the balloon chamber thereof,
i) reducing the pressure in said second balloon catheter and withdrawing fluid from and thereby collapsing the balloon chamber thereof, and
j) removing said first balloon catheter and said second balloon catheter from said passageway.

14. A method for performing a medical procedure involving enlarging the flow passage of a section of a fluid passageway within the patient's body comprising:

a) placing a first, relatively small diameter balloon catheter in said passageway;
   said first balloon catheter having a catheter portion and a balloon portion and a proximal end and a distal end, with said balloon portion located at or near said distal end,
   said first balloon catheter having a fitting at or near its proximal end for connection thereto of fluid pressure application means, said first balloon catheter further having a captive safety guide,
b) advancing said first balloon catheter through said passageway until said balloon portion is located within said section to be enlarged,
c) expanding the balloon portion of said first balloon catheter by forcing fluid under pressure through the catheter portion thereof into the balloon chamber,
d) reducing the pressure in said first balloon catheter and withdrawing fluid from and thereby collapsing said first balloon chamber prior to feeding said second balloon portion into said passageway section,
e) removing said fitting from said first balloon catheter,
f) placing a second, larger diameter balloon catheter over the catheter portion of said first balloon catheter,
   said second balloon catheter having a catheter portion and balloon portion and a proximal end and a distal end, with said balloon portion located at or near said distal end,
   said second balloon catheter further having sliding guide means near said distal end, which sliding guide means is so sized and positioned as to accommodate therein and permit sliding passage therethrough of the balloon portion and the catheter portion of said first balloon catheter,
   said sliding guide means being further characterized in that it has a distal end and a proximal end and is not longer than about ½ the overall length of said second balloon catheter,
g) feeding the proximal end of the catheter portion of said first balloon catheter through said sliding guide means, from the distal end thereof to the proximal end thereof, and continuing to feed said second balloon catheter into said passageway and along said first balloon catheter until said balloon portion of said second balloon catheter is within the passageway section to be enlarged,
h) expanding the balloon portion of said second balloon catheter by forcing fluid under pressure through the catheter portion thereof into the balloon chamber thereof,
i) reducing the pressure in said second balloon catheter and withdrawing fluid from and thereby collapsing the balloon chamber thereof, and
j) removing said first balloon catheter and said second balloon catheter from said passageway.

15. A method for performing a medical procedure involving enlarging the flow passage of a section of a fluid passageway within the patient's body comprising:

a) placing a first, relatively small diameter balloon catheter in said passageway;
   said first balloon catheter having a catheter portion and a balloon portion and a proximal end and a distal end, with said balloon portion located at or near said distal end, said first balloon catheter having a fitting at or near its proximal end for connection thereto of fluid pressure application means,
b) advancing said first balloon catheter through said passageway until said balloon portion is located within said section to be enlarged,
c) expanding the balloon portion of said first balloon catheter by forcing fluid under pressure through the catheter portion thereof into the balloon chamber,
d) reducing the pressure in said first balloon catheter and withdrawing fluid from and thereby collapsing said first balloon chamber prior to feeding said second balloon portion into said passageway section,
e) removing said fitting from said first balloon catheter,
f) placing a second, larger diameter balloon catheter over the catheter portion of said first balloon catheter,
said second balloon catheter having a catheter portion and balloon portion and a proximal end and a distal end, with said balloon portion located at or near said distal end,
said second balloon catheter further having sliding guide means comprised of a ring at said distal end of said second balloon catheter, which sliding guide means is so sized and positioned as to accommodate therein and permit sliding passage therethrough of the balloon portion and the catheter portion of said first balloon catheter,
said sliding guide means being further characterized in that it has a distal end and a proximal end and is not longer than about ½ the overall length of said second balloon catheter,
g) feeding the proximal end of the catheter portion of said first balloon catheter through said sliding guide means, from the distal end thereof to the proximal end thereof, and continuing to feed said second balloon catheter into said passageway and along said first balloon catheter until said balloon portion of said second balloon catheter is within the passageway section to be enlarged,
h) expanding the balloon portion of said second balloon catheter by forcing fluid under pressure through the catheter portion thereof into the balloon chamber thereof,
i) reducing the pressure in said second balloon catheter and withdrawing fluid from and thereby collapsing the balloon chamber thereof, and
j) removing said first balloon catheter and said second balloon catheter from said passageway.

16. A method for performing a medical procedure involving enlarging the flow passage of a section of a fluid passageway within the patient's body comprising:
a) placing a first, relatively small diameter balloon catheter in said passageway;
said first balloon catheter having a catheter portion and a balloon portion and a proximal end and a distal end, with said balloon portion located at or near said distal end,
said first balloon catheter having a fitting at or near its proximal end for connection thereto of fluid pressure application means,
b) advancing said first balloon catheter through said passageway until said balloon portion is located within said section to be enlarged,
c) expanding the balloon portion of said first balloon catheter by forcing fluid under pressure through the catheter portion thereof into the balloon chamber,
d) reducing the pressure in said first balloon catheter and withdrawing fluid from and thereby collapsing said first balloon chamber prior to feeding said second balloon portion into said passageway section,
e) removing said fitting from said first balloon catheter,
f) placing a second, larger diameter balloon catheter over the catheter portion of said first balloon catheter,
said second balloon catheter having a catheter portion and balloon portion and a proximal end and a distal end, with said balloon portion located at or near said distal end,
said second balloon catheter further having sliding guide means comprised of a flexible loop at said distal end of said second balloon catheter, which sliding guide means is so sized and positioned as to accommodate therein and permit sliding passage therethrough of the balloon portion and the catheter portion of said first balloon catheter,
said sliding guide means being further characterized in that it has a distal end and a proximal end and is not longer than about ½ the overall length of said second balloon catheter,
g) feeding the proximal end of the catheter portion of said first balloon catheter through said sliding guide means, from the distal end thereof to the proximal end thereof, and continuing to feed said second balloon catheter into said passageway and along said first balloon catheter until said balloon portion of said second balloon catheter is within the passageway section to be enlarged,
h) expanding the balloon portion of said second balloon catheter by forcing fluid under pressure through the catheter portion thereof into the balloon chamber thereof,
i) reducing the pressure in said second balloon catheter and withdrawing fluid from and thereby collapsing the balloon chamber thereof, and
j) removing said first balloon catheter and said second balloon catheter from said passageway.

17. The method of claim 16 wherein said flexible loop is of variable size at the distal end of said second balloon catheter.

* * * * *

UNITED STATES PATENT AND TRADEMARK OFFICE
CERTIFICATE OF CORRECTION

PATENT NO.   : 5,180,367
DATED        : January 19, 1993
INVENTOR(S)  : STAVROS B. KONTOS, ET AL.          Page 1 of 2

It is certified that error appears in the above-identified patent and that said Letters Patent is hereby corrected as shown below:

COLUMN 1

Line 13, "cross sectional" should read --cross-sectional--.

COLUMN 3

Line 2, "multilumen" should read --multi-lumen--.

COLUMN 4

Line 19, "cross sectional" should read --cross-sectional--.
Line 45, "cross sectioned" should read --cross-sectioned--.
Line 47, "cross sectioned" should read --cross-sectioned--.
Line 64, "fluid tight" should read --fluid-tight--.

COLUMN 5

Line 44, "tube 12" should read --tube 22--.
Line 46, "tube 12" should read --tube 22--.

COLUMN 6

Line 20, "42," should read --42--.

COLUMN 9

Line 44, "than" should read --then--.

COLUMN 10

Line 14, "end, in" should read --end;--.
Line 15 should be deleted.
Line 22, "end," should read --end;--.

UNITED STATES PATENT AND TRADEMARK OFFICE
CERTIFICATE OF CORRECTION

PATENT NO. : 5,180,367
DATED      : January 19, 1993
INVENTOR(S): STAVROS B. KONTOS, ET AL.

It is certified that error appears in the above-identified patent and that said Letters Patent is hereby corrected as shown below:

COLUMN 11

Line 17, "said fitting" should read --said fitting means--.
   Line 23, "chamber" should read --catheter--.
   Line 26, "chamber" should read --catheter--.
   Line 28, "chamber." should read --catheter.--.

COLUMN 12

Line 26, "from said" should read --in a-- and
            "said fluid" should read --a fluid--.
   Line 39, "catheter;" should read --catheter,--.
   Line 59, "claim 9" should read --claims 8 or 9--.

Signed and Sealed this

Twenty-second Day of February, 1994

Attest:

BRUCE LEHMAN

*Attesting Officer*     *Commissioner of Patents and Trademarks*